(12) United States Patent
Sogaro

(10) Patent No.: US 7,861,897 B2
(45) Date of Patent: Jan. 4, 2011

(54) APPLICATOR DEVICE

(75) Inventor: Alberto C. Sogaro, Kronberg (DE)

(73) Assignee: Dentaco Dentalindustrie-und Marketing GmbH, Bad Homburg (DE)

( * ) Notice: Subject to any disclaimer, the term of this patent is extended or adjusted under 35 U.S.C. 154(b) by 1096 days.

(21) Appl. No.: 11/590,585

(22) Filed: Oct. 31, 2006

(65) Prior Publication Data

US 2007/0108235 A1    May 17, 2007

(30) Foreign Application Priority Data

Nov. 3, 2005   (EP)   ................... 05023994

(51) Int. Cl.
*B65D 37/00* (2006.01)
*B43M 11/06* (2006.01)

(52) U.S. Cl. .............. 222/209; 222/633; 222/213; 401/183; 401/186

(58) Field of Classification Search .......... 222/206, 222/209, 213, 214, 215, 633, 631, 632; 401/183, 401/184, 185, 186
See application file for complete search history.

(56) References Cited

U.S. PATENT DOCUMENTS

| | | | |
|---|---|---|---|
| 3,563,415 A | * | 2/1971 | Ogle ............ 222/145.4 |
| 3,722,512 A | * | 3/1973 | Hein et al. ............ 604/231 |
| 4,657,534 A | | 4/1987 | Beck et al. |
| 4,741,737 A | | 5/1988 | Meyer et al. |
| 4,941,876 A | | 7/1990 | Meyer et al. |
| 6,447,476 B1 | | 9/2002 | Sogaro |
| 6,719,729 B2 | | 4/2004 | Sogaro |
| 7,131,784 B2 | * | 11/2006 | Lee et al. ............ 401/128 |

FOREIGN PATENT DOCUMENTS

DE   20019091   5/2001

* cited by examiner

*Primary Examiner*—Kevin P Shaver
*Assistant Examiner*—Stephanie E Williams
(74) *Attorney, Agent, or Firm*—Quarles & Brady LLP

(57) ABSTRACT

An applicator device for a free-flowing substance includes a carrier body provided with an application device at one end and a pin at an opposing end. A transverse channel penetrates the pin, and an axial channel branching off from the transverse channel leads to the application device. A reservoir device having a ring-shaped edge seal sealingly engages the pin, whereby the applicator device is activated by displacing the reservoir device on the pin toward the application device to open a flow connection between the reservoir device and the transverse channel. The reservoir device has a receptacle segment that is elastically deformable at least in portions so that, when the applicator device is activated and a flow connection between the transverse channel and the receptacle segment exists, the free-flowing substance is discharged via the application device by manual compression of the elastically deformable area of the receptacle segment.

17 Claims, 4 Drawing Sheets

APPLICATOR DEVICE

CROSS REFERENCES TO RELATED APPLICATIONS

This application claims the priority benefit of European Patent Application No. 05 023 994.6 filed on Nov. 3, 2005.

STATEMENT REGARDING FEDERALLY SPONSORED RESEARCH

Not Applicable.

DESCRIPTION OF THE BACKGROUND ART

This invention relates to an applicator device for a free-flowing substance comprising a carrier body which is provided with an application device and which, on the side farther from the application device, has a cylindrical pin which is penetrated by a transverse channel from which an axial channel branches off and leads to the application device. On the cylindrical pin there is a reservoir device that is used to hold the free-flowing substance and has at least one ring-shaped edge seal that is located on the inside and interacts in a sealing manner with the cylindrical pin of the carrier body. The applicator device is activated by pushing the reservoir device on the cylindrical pin in the direction of the application device.

An applicator device of this type is described in DE 200 19 091 U1 and is used in particular for the application of pharmaceutical or cosmetic substances onto the human body. The applicator device of the prior art is realized in the form of a mini-syringe and, as the application device, has a tip in the form of a hollow needle, by means of which the free-flowing substance can be deposited. For activation, the reservoir device, which is realized in the shape of a pot or in the form of a tube that is closed on one end, is pushed manually on the cylindrical pin so that the pin acts like a piston which displaces the free-flowing substance stored in the reservoir device, whereby the free-flowing substance flows through the transverse channel and the axial channel of the carrier body to the application tip. During the activation, the side wall of the reservoir device is displaced into a ring-shaped recess that surrounds the cylindrical pin.

Unfortunately a controlled pushing of the test-tube shaped reservoir device on the cylindrical pin turns out to be difficult. As a result, the applicator device described in DE 200 19 091 U1 has the disadvantage that the precision dosing of the free-flowing substance is not easily possible.

SUMMARY OF THE INVENTION

The object of the invention is to create an applicator device having an improved dosing characteristics compared to similar devices of the prior art. This object is accomplished in one embodiment by providing an applicator device for a free-flowing substance including a carrier body which is provided with an application device and which, on one end farthest from the application device has a cylindrical pin which is penetrated by a transverse channel, from which an axial channel branches off, which leads to the application device, whereby on the cylindrical pin a reservoir device can be displaced which on its inside has a ring-shaped edge seal which interacts in a sealed manner with the cylindrical pin, whereby the applicator device is activated by the displacement of the reservoir device on the cylindrical pin toward the application device to open a flow connection between the reservoir device and the transverse channel, characterized in that the reservoir device has a receptacle segment that is elastically deformable at least in portions so that, when a flow connection between the transverse channel and the receptacle segment exists in the activation position of the applicator device, the free-flowing substance is discharged via the application device by manual compression of the elastically deformable area of the receptacle segment.

Accordingly, the invention consists of the fact that the reservoir device has a receptacle segment that is elastically deformable at least in sections and, in the activation position of the applicator device in which the edge seal is located on the side of the openings of the transverse channel of the cylindrical pin farther from the reservoir segment and thus establishes a flow connection between the receptacle segment and the transverse channel, can be compressed manually so that the free-flowing substance is deposited by means of the applicator device.

The principle of the applicator device incorporating the invention is therefore that after the activation, i.e. after the reservoir device has been pushed on the cylindrical pin, the free-flowing substance is discharged via the application device by manually applying pressure to the side of the receptacle segment. No further displacement of the application device on the cylindrical pin is required for this purpose. Therefore the pin does not act as a displacement piston for the free-flowing substance.

The applicator device claimed by the invention is suitable in particular for the application of pharmaceutical or cosmetic substances to a human or animal body and for this purpose can be provided with an application device that is adapted to the respective application. For example, the application device can be a pipette tip or can also include a brush or a sponge. Pharmaceutical substances that can be applied using the device claimed by the invention include, for example a tissue adhesive, a dental adhesive or a similar substance.

The applicator device claimed by the invention is designed in particular in the form of a disposable device in which the reservoir device is pre-filled. In the deactivated state representing a closed position, the free-flowing substance is held in the reservoir device and is retained by the edge seal. This status is generally the as-delivered status of the applicator device. To activate the applicator device, all that is required of the user is a telescoping compression of the carrier body and of the reservoir device of the applicator device, thereby effecting a transition from the closed storage position into the open dispensing position of the application device with reference to the carrier body. During the activation, the edge seal brushes over the openings of the transverse channel in the pin.

The receptacle segment of the reservoir device can be realized in a wide variety of ways. For example, the receptacle segment can be in the shape of a bubble, a test tube, a collapsing tube, a sphere or a bulb.

The reservoir device of the applicator device claimed by the invention can comprise one or more receptacle bodies. In the latter case, one component of a multiple-component system can be contained in each of the bodies. When the applicator device is activated, it is necessary to create a flow connection between the receptacle bodies of the reservoir device, so that the mixed multiple-component system is located in a chamber of the reservoir device which is surrounded by an elastically deformable wall of the receptacle segment which characterizes the receptacle segment for the application of the free-flowing substance. Then, after the compression of the receptacle segment, the mixed multiple-component system can be transported to the transverse channel and from there via the axial channel to the application device.

In one special realization of the applicator device claimed by the invention, the receptacle bodies of a reservoir device that has a plurality of receptacle bodies can be telescoped to create a flow connection. In this case, preferably one of the receptacle bodies has a cylindrical segment which on the inside has an edge seal which interacts with a cylindrical peripheral surface of the other receptacle body on which transverse openings are realized. When the edge seal travels over the transverse openings, a flow connection between the receptacle bodies is created.

It is further conceivable that the applicator device comprises two reservoir devices that are located next to each other, each of which is located on a cylindrical pin which is realized in the manner described above. In that case, the carrier body has two essentially parallel axial channels, downstream of which a static mixer can be located.

Additional advantages and advantageous configurations of the object of the invention are described and illustrated in greater detail below, in the accompanying drawing and in the claims.

BRIEF SUMMARY OF THE DRAWINGS

Six exemplary embodiments of an applicator device claimed by the invention are illustrated schematically and in a simplified manner in the accompanying drawings and are described in greater detail below. In the drawings:

FIG. 4 shows an alternative embodiment of a reservoir device of an applicator device of the type illustrated in FIG. 1;

DETAILED DESCRIPTION OF THE PREFERRED EMBODIMENTS

Figure 1:
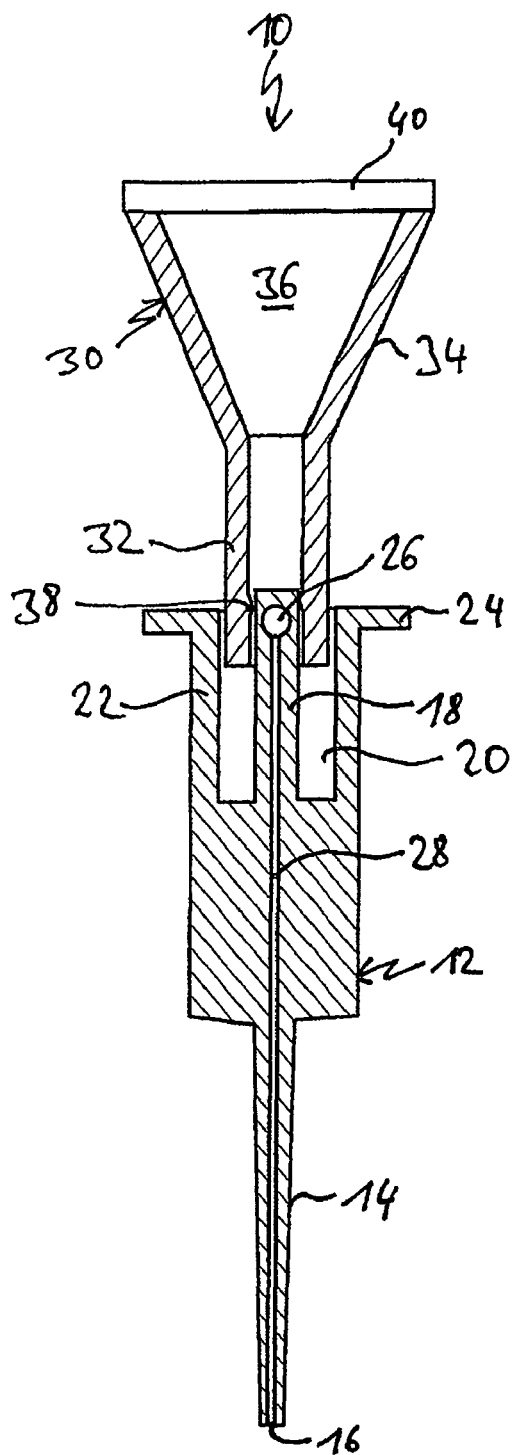
FIG. 1 is a longitudinal section through a first embodiment of an applicator device for a single-component system in the deactivation position.
Figure 2:
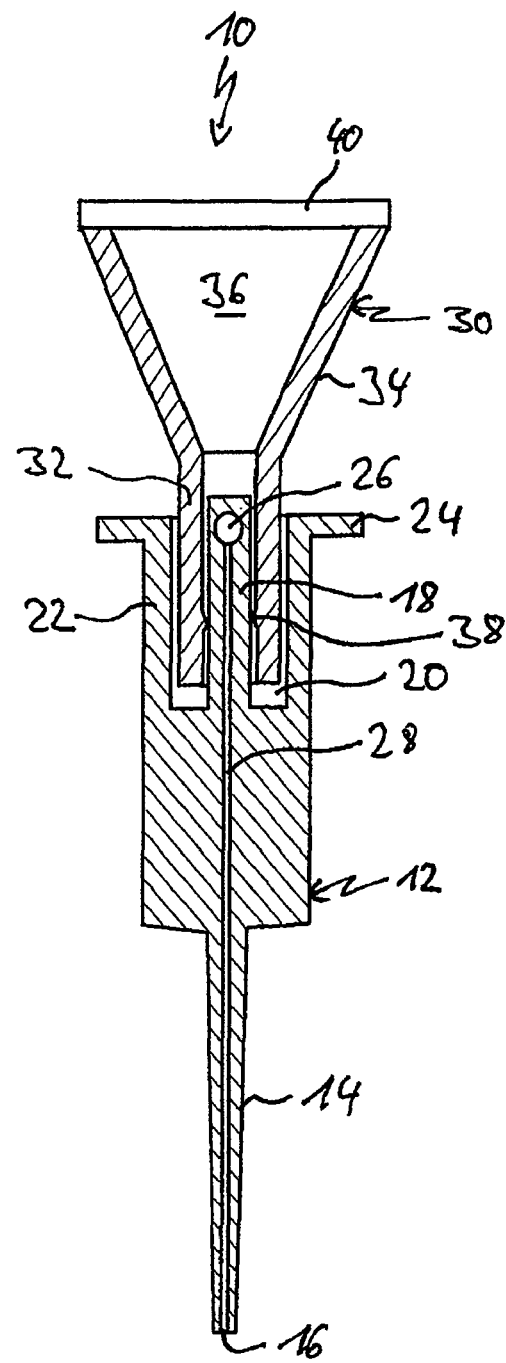
FIG. 2 shows the applicator device illustrated in FIG. 1 in the activation position.

FIGS. 1 and 2 show an applicator device 10 which is used, for example, for the dispensing of a free-flowing substance via a pipette and comprises a carrier body 12, on which an application device 14 that is realized in the form of a syringe is molded in one piece. The application device 14 has a discharge opening 16 for the free-flowing substance on its exposed end surface.

On the side farther from the application device 14, the carrier body 12 has a cylindrical, piston-like pin 18 which is surrounded by a ring-shaped recess 20, which is in turn bordered on the outside by a peripheral wall 22. A collar 24 that acts as a gripping aid is in turn molded onto the peripheral wall 22. In the terminal area opposite from the application device 14, the pin 18 is penetrated by a transverse channel 26 that extends in the radial direction. From the transverse channel 26, an axial channel 28 which lies in the axis of the pin 18 in turn branches off and runs to the discharge opening 16 of the application device 14.

The applicator device 10 further comprises a reservoir device 30 in which the free-flowing substance can be stored. The reservoir device 30 comprises a tube-shaped guide segment 32 and a receptacle segment 34 that is adjacent to the side farthest from the application device 14. The receptacle segment 34 defines a receptacle chamber 36 for the free-flowing substance. The guide segment 32, on its inside, has a ring-shaped edge seal 38, which is located so that it can slide on the peripheral surface of the cylindrical pin 18. The receptacle segment 36 is realized in the shape of a tube and has a sealing seam 40 in its terminal area farther from the pin 18. The reservoir device 30 is fabricated from an elastically deformable material so that the receptacle segment 34 can be compressed manually.

In the position of the reservoir device 30 illustrated in FIG. 1, the edge seal 38 is located in a terminal area of the peripheral surface of the pin 18, so that the flow of the fluid between the receptacle chamber 36 and the transverse channel 26 is blocked. For the activation of the applicator device 10, the reservoir device 30 is moved into its open dispensing position which is illustrated in FIG. 2. During this process, the edge seal 38 passes over the transverse channel 26 so that a flow connection between the receptacle chamber 36 and the transverse channel 26 is created via an annular gap between the cylindrical pin 18 and the guide segment 32 of the reservoir device 30. As the result of manual pressure which is applied to the side of the receptacle segment 34, the free-flowing substance contained in the receptacle chamber 36 can be displaced out of the receptacle chamber 36 and transported via the transverse channel 26 and the axial channel 28 to the discharge opening 16 of the application device 14 and applied.

Figure 4:
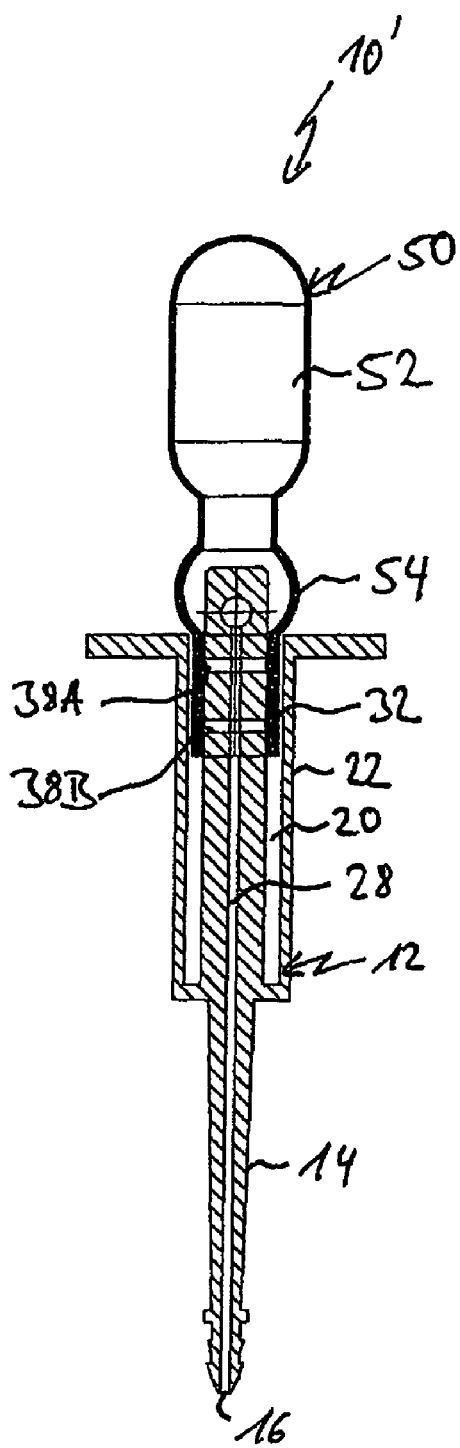
FIG. 4 shows the applicator device illustrated in FIG. 3 in the activation position.
Figure 3:
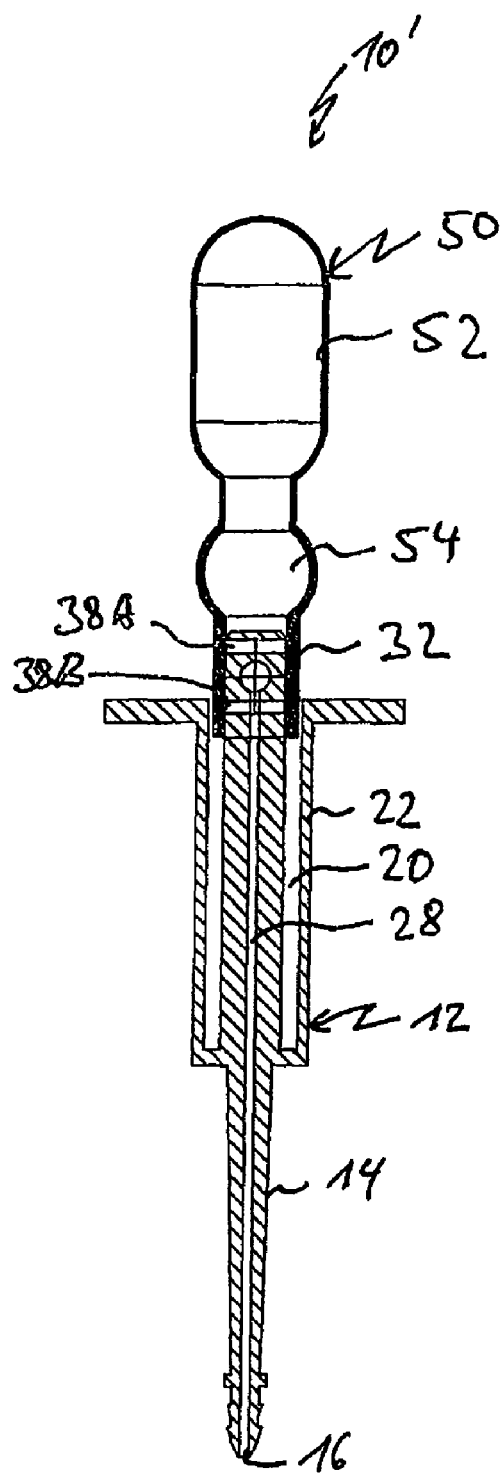
FIG. 3 is a longitudinal section through a second embodiment of an applicator device for a single-component system in the deactivation position.

FIGS. 3 and 4 show an alternative realization of an applicator device 10', which comprises a reservoir device 50 which, instead of the reservoir device illustrated in FIG. 1, can be placed on a carrier body 12 of the type illustrated in FIG. 1. The reservoir device 50 comprises a tubular guide segment 32 which on the inside has two ring-shaped edge seals 38A and 38B which interact with the cylindrical pin 18 of the carrier body 12. On the end farther from the edge seals 38A and 38B, a bubble-like receptacle segment 52 is adjacent to the guide segment 32, which receptacle segment 52 contains a free-flowing substance to be applied and is elastically compressible.

In a middle area of the guide segment 32, there is also a widened area 54, which in the activation position of the reservoir device 50 is located on the cylindrical pin of the carrier body 12 at the level of its transverse channel 26. Advantageously, the widened area 54 improves the flow behavior of the free-flowing substance and acts as a stop during the activation of the applicator device 10'. The function of the reservoir device 50 and its interaction with the carrier body 18 correspond to the realization illustrated in FIGS. 1 and 2.

Figure 5:
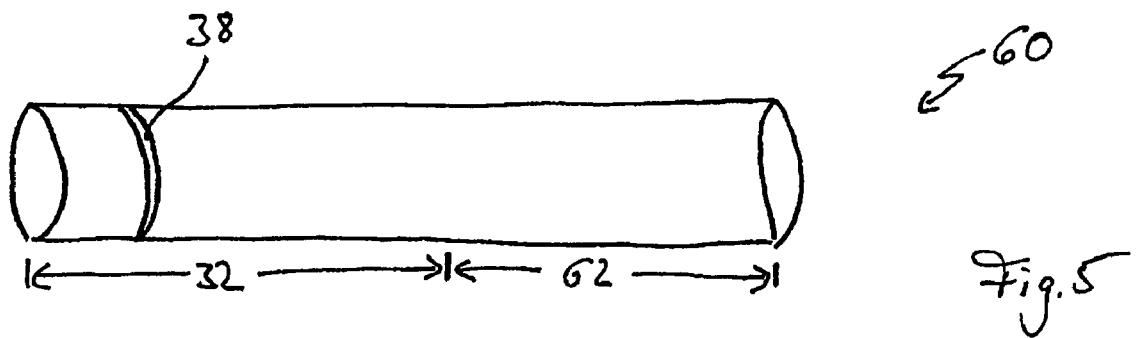
FIG. 5 shows an additional embodiment of a reservoir device.

FIG. 5 shows an additional embodiment of a reservoir device 60 which can be used in connection with a carrier body 12 of the type illustrated in FIG. 1. The reservoir device 60 is formed from an elastically deformable small tube that has one open end and one closed end. In the vicinity of the open end, located on the inside of the small tube is an edge seal 38 which, corresponding to the embodiments illustrated in FIGS. 1 to 3, interacts with the cylindrical pin of the carrier body and is associated with a guide segment 32 of the reservoir device 60. The reservoir device 60 is longer than the cylindrical pin 18 of the associated carrier body 12 of the applicator device, so that even in the activated state of the applicator device, a receptacle segment 62 remains connected to the guide segment 32, in which receptacle segment 62 the free-flowing substance is located after the activation of the applicator device in question. The free-flowing substance is thereby not expelled from the reservoir device 60 by a piston action of the pin 18 of the carrier body 12. The receptacle segment 62 can instead be compressed by lateral pressure applied manually, as a result of which the free-flowing substance is transported through the transverse channel 26 and the axial channel 28 of the carrier body 12 to the application device 14 and is applied by means of the application device.

Figure 6:
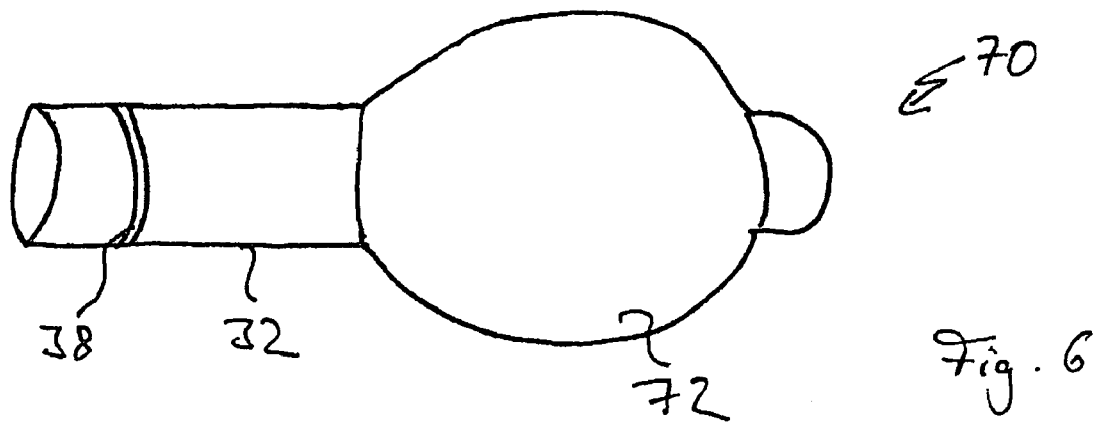
FIG. 6 shows a fourth embodiment of a reservoir device.

FIG. 6 illustrates an additional embodiment of a reservoir device 70 which differs from the reservoir devices illustrated in FIGS. 1 and 2 only in that instead of a tube-shaped receptacle segment 72 it has a bubble-shaped receptacle segment 72.

Figure 7:
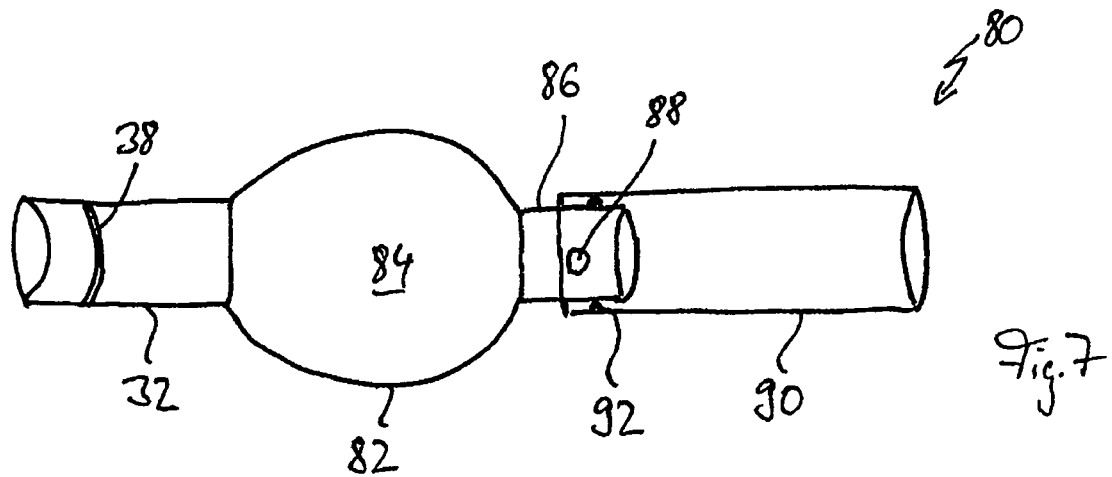
FIG. 7 shows a reservoir device with a plurality of receptacle chambers.

FIG. 7 illustrates a reservoir device 80 which is also designed for use in connection with a carrier body 12 of the type illustrated in FIG. 1. The reservoir device 80 is designed for a two-component system, the individual components of which are combined with each other only immediately prior to application. For this purpose, the reservoir device 80 comprises a first receptacle body 82 with a guide segment 32 for interaction with the cylindrical pin 18 of the carrier body 12 in the manner described in connection with FIG. 1. The receptacle body 82 also has a receptacle segment 84 in which one component of the two-component system is contained prior to mixing. The receptacle segment 84 is realized so that it is elastically compressible. On the side farther from the guide segment 32, the receptacle body 82 has an additional guide segment 86 which is provided with transverse openings 88 on its peripheral surface and is closed on its end. On the guide segment 86 sits a pot-shaped second receptacle body 90 which is guided so that it slides with its terminal area farther from the base on the guide segment 86, and in this area has an inner edge seal 92.

For the activation, the second receptacle body 90 is telescoped toward the first receptacle body 82 so that a flow connection between the interior of the second receptacle body 90 and the interior of the first receptacle body 82 is created via an annular gap between the guide segment 86 of the first receptacle body 82 and the second receptacle body 90 and the transverse openings 88. The substance in the second receptacle segment 90 can thus flow into the first receptacle body 82, where it can be mixed with the other component of the two-component system.

As a result of an appropriate displacement of the reservoir device 80 on the cylindrical pin 18 of the carrier body 12, a flow connection is then also created between the transverse channel 26 of the carrier body 12 and the receptacle chamber of the receptacle segment 84. Then, by manual compression of the receptacle segment 84, the two-component system can be applied by means of the application device 14.

Figure 8:
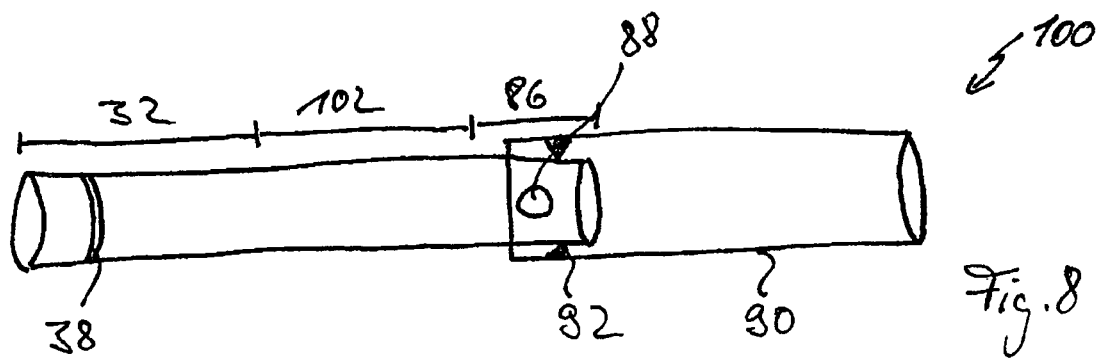
FIG. 8 shows an alternative embodiment of a reservoir device with a plurality of receptacle chambers.

The embodiment of a reservoir device 100 illustrated in FIG. 8 corresponds essentially to the embodiment of the reservoir device illustrated in FIG. 6, and differs from the latter only in that the first receptacle body 82 is realized in the manner of a small tube that is closed on one end, which comprises both the guide segment 32 as well as a receptacle segment 102 that is adjacent to the guide segment 32 and is laterally compressible.

Figure 9:
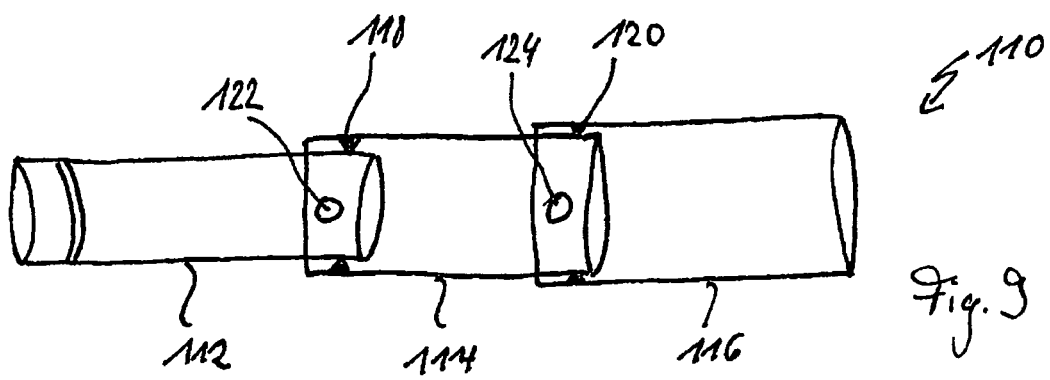
FIG. 9 shows a last embodiment of a reservoir device with a plurality of receptacle chambers.

FIG. 9 illustrates a reservoir device 110 which is also realized for the separate storage of two components of a two-component system. The reservoir device 110 has three sections 112, 114 and 116, each of which is realized in the form of a small tube with an open end and a closed end. In the vicinity of the open end, on the inside of each of the tubes 112, 114 and 116 there is an edge seal 38, 118 and 120 respectively, each of which interacts with the peripheral surface of the carrier body 12 or of the neighboring part 112 or 114 to open the transverse channel 26 of the pin 18 of the carrier body 12 or transverse openings 122 and 124 respectively of the neighboring section 112 or 114.

At least the section 112 is realized so that it can be compressed in the transverse direction, so that the component of the two-component mixture that is contained in this section 112 can be displaced by manual pressure on this section 112 from the reservoir device 110 and can be applied via the carrier body 12 and the application device 14.

I claim:

1. An applicator device for a free-flowing substance comprising:
   a carrier body provided with an application device at one end and a pin at an opposing end;
   a transverse channel penetrating the pin;
   an axial channel branching off from the transverse channel and leading to the application device; and
   a reservoir device having a ring-shaped edge seal sealingly engaging the pin, said pin being fully extendible into only a portion of said reservoir device, whereby the applicator device is activated by fully extending said pin into the reservoir device toward the application device to open a flow connection between the reservoir device and the transverse channel without discharging the free-flowing substance via the application device, the reservoir device having a receptacle segment that is sufficiently elastically deformable at least in portions so that, when the applicator device is activated and a flow connection between the transverse channel and the receptacle segment exists, the free-flowing substance is discharged via the application device by manual compression of the elastically deformable area of the receptacle segment.

2. The applicator device as in claim 1, in which the elastically deformable area of the receptacle segment is in the form of a bubble.

3. The applicator device as in claim 1, in which the elastically deformable area of the receptacle segment is in the form of a small tube.

4. The applicator device as in claim 1, in which the elastically deformable area of the receptacle segment is in the form of a collapsible tube.

5. The applicator device as in claim 1, in which the reservoir device includes a guide segment having a widened area which during activation of the applicator device lies at the level of the transverse channel of the pin.

6. The applicator device as in claim 1, in which the reservoir device includes at least two receptacle bodies, one for each component of a multiple-component system.

7. The applicator device as in claim 6, in which the at least two receptacle bodies can be telescoped to create a flow connection, whereby at least one of the receptacle bodies has, on its inside, an edge seal which interacts with a peripheral surface of the other receptacle body.

8. The applicator device as in claim 1, in which the pin has at least one annular groove which interacts with the edge seal and defines a deactivation position and/or an activation position of the receptacle device.

9. The applicator device as in claim 1, in which the pin is cylindrical.

10. Applicator device for a free-flowing substance comprising a carrier body which is provided with an application device and which, on the end farther from the application device has a cylindrical pin which is penetrated by a transverse channel, from which an axial channel branches off, which leads to the application device, whereby the cylindrical pin can be fully extended into only a portion of a reservoir device, which on its inside has a ring-shaped edge seal which interacts in a sealed manner with the cylindrical pin, whereby the applicator device is activated by fully extending the cylindrical pin into the reservoir device toward the application device to open a flow connection between the reservoir device and the transverse channel without discharging the free-flowing substance via the application device, characterized in that the reservoir device has a receptacle segment that is sufficiently elastically deformable at least in portions so that, when a flow connection between the transverse channel and the receptacle segment exists in the activation position of the applicator device, the free-flowing substance is discharged via the application device by manual compression of the elastically deformable area of the receptacle segment.

11. Applicator device as recited in claim 10, characterized in that the elastically deformable area of the receptacle segment is realized in the form of a bubble.

12. Applicator device as recited in claim 10, characterized in that the elastically deformable area of the receptacle segment is realized in the form of a small tube.

13. Applicator device as recited in claim 10, characterized in that the elastically deformable area of the receptacle segment is realized in the form of a collapsible tube.

14. Applicator device as recited in claim 10, characterized in that the guide segment has a widened area which during the activation of the applicator device lies at the level of the transverse channel of the pin.

15. Applicator device as recited in claim 10, characterized in that the reservoir device comprises at least two receptacle bodies, one for each component of a multiple-component system.

16. Applicator device as recited in claim 15, characterized in that the at least two receptacle bodies can be telescoped for the creation of a flow connection, whereby at least one of the receptacle bodies has, on the inside, an edge seal which interacts with a peripheral surface of the other receptacle body.

17. Applicator device as recited in claim 10, characterized in that the cylindrical pin has at least one annular groove which interacts with the edge seal and defines a deactivation position and/or an activation position of the receptacle device.

* * * * *